United States Patent [19]

Mozsary

[11] Patent Number: 4,552,532
[45] Date of Patent: Nov. 12, 1985

[54] OSTEOCORRECTIVE DENTOALVEOLAR IMPLANT SYSTEM

[76] Inventor: Peter G. Mozsary, 413 Skyline Drive, Vallejo, Calif. 94590

[21] Appl. No.: 560,199

[22] Filed: Dec. 12, 1983

[51] Int. Cl.$^4$ ............................................... A61C 8/00
[52] U.S. Cl. ..................................... 433/173; 433/174
[58] Field of Search ............... 433/173, 174, 175, 176, 433/169

[56] References Cited

U.S. PATENT DOCUMENTS

| | | | |
|---|---|---|---|
| 3,827,145 | 8/1974 | Richards | 433/175 |
| 3,934,347 | 1/1976 | Lash et al. | 433/180 |
| 3,955,280 | 5/1976 | Sneer | 433/174 |
| 4,416,629 | 11/1983 | Mozsary et al. | 433/173 |
| 4,447,210 | 5/1984 | Hidaka et al. | 433/173 |

FOREIGN PATENT DOCUMENTS

| | | | |
|---|---|---|---|
| 3110693 | 9/1982 | Fed. Rep. of Germany | 433/174 |
| 1305478 | 1/1973 | United Kingdom | 433/173 |

Primary Examiner—Wilson: John J.
Attorney, Agent, or Firm—Bielen & Peterson

[57] ABSTRACT

A dental implant system utilizing a root which is fixed to the jawbone. A post is supported to the root and has a crown connected thereto. A member is provided for cushioning forces applied to the crown and a stop is also included to limit the movement between the crown and the root upon the application of force to the crown.

9 Claims, 3 Drawing Figures

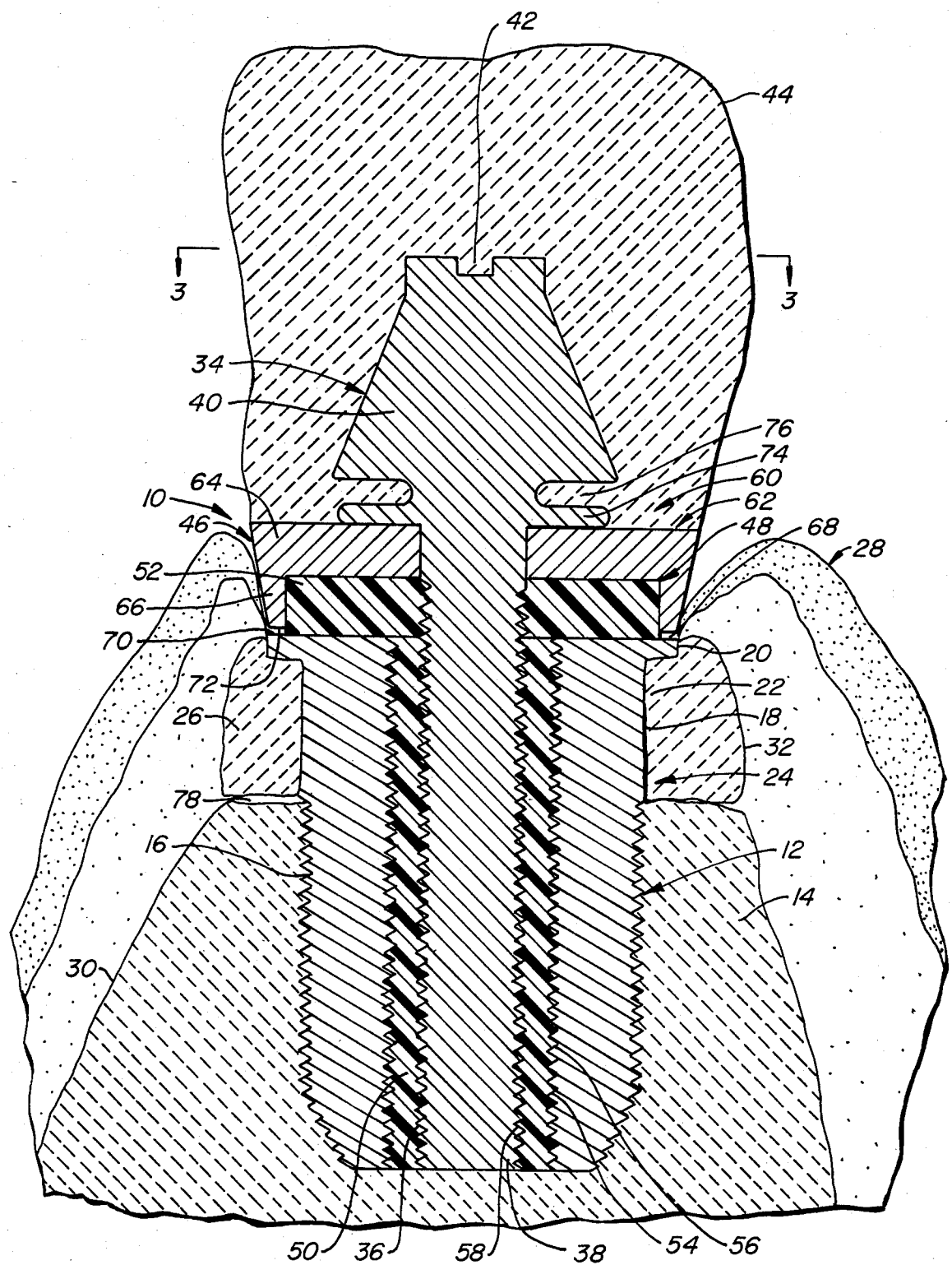
FIG.—1.

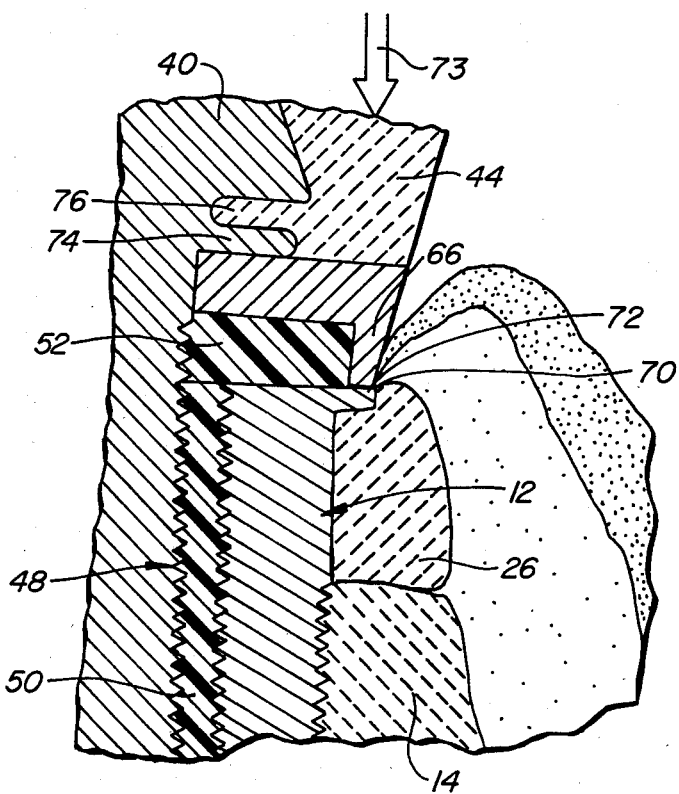
FIG._2.
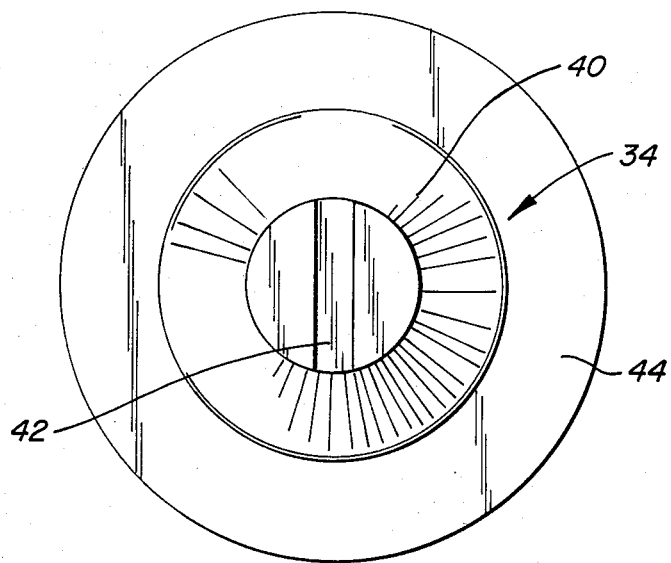
FIG._3.

OSTEOCORRECTIVE DENTOALVEOLAR IMPLANT SYSTEM

BACKGROUND OF THE INVENTION

The present invention relates to a novel dental implant system which very closely mimics the characteristics of a natural tooth. Dental implants have become quite successful in many aspects. The problems of chronic infection and bone loss have been generally overcome by the use of a two stage implant such as those described in U.S. Pat. Nos. 3,589,011 and 4,416,629. There still remain problems concerning traumatic damage to the jawbone resulting in the loss of the implant and loss of teeth. U.S. Pat. No. 4,416,629 describes an implant having a superstructure with a weakened portion to protect the implant and the adjacent teeth against damages resulting from forces which overload the implant system. U.S. Pat. No. 3,955,280 addresses the problem of shock absorption by the use of a spring placed within the implant. U.S. Pat. No. 4,270,905 employs an elastic material which attaches directly to the jawbone to absorb the masticatory load.

None of the prior implant systems provides for limiting the mobility of the artificial tooth in the same manner and to the same extend as a natural tooth. An implant system which closely mimics the natural tooth in shock absorbing and mobility characteristics would be a great advance in the dental field.

SUMMARY OF THE INVENTION

In accordance with the present invention a novel and useful dental implant system closely resembling a natural tooth is provided.

The implant system of the present invention utilizes a root having means for fixing the root to the jawbone. A post is also included and has means for supporting the same to the root. A crown or superdenture connects to the post.

Means is also provided in the implant of the present invention for cushioning forces applied to the crown during masticatory activity. The force cushioning means may take the form of a resilient member having a portion placed between the post and the root.

The implant may also include means for attenuating relative movement between the crown and the root upon the application of force to the crown. Such means may take the form of a spacer disposed adjacent the means for cushioning forces applied to the crown. The relative movement attenuating means may take the form of a spacer placed adjacent a resilient member. In this case, the root may include a first surface and the spacer may include a second surface such that the first and second surfaces are capable of contacting one another. The resilient member could be formed into a first portion placed between the crown and the resilient member and a second portion which lies closer to the root than the first portion thereof. The spacer second portion would provide the heretofore described second surface which is capable of touching the first surface provided by the root. The spacer may be assembled such that its second portion lies apart from the root i.e. the first surface of the root and the second surface of the second portion of the spacer do not touch, when no force is acting on the crown. Also, the interposed resilient member would permit the second portion of the spacer to travel toward the root resulting in the engagement of the first and second surfaces of the root and second portion of the spacer respectively when force is applied to the crown. The gap between the first surface of the root and the second surface of the second portion of the spacer may be predetermined to follow the mobility found in the natural tooth.

The present implant system may also embrace forming the post with a flange which lies adjacent the spacer. The post may be movable in relation to the root which causes relative movement between the post and the spacer.

Moreover, the present implant system may encompass means for holding artificial bone material to the root. Such artificial bone would replace a segment of the jawbone missing subsequent to the extraction of the natural tooth before the implantation of the artificial tooth. The means for holding the artificial bone may include a concave chamber formed about the exterior of the root.

It may be apparent that a novel and useful dental implant system has been described.

It is therefore an object of the present invention to provide a dental implant system which is permanently placed in the jawbone and which possesses the functions of a natural tooth after implantation.

It is another object of the present invention to provide a dental implant system which includes a structural provision for replacement for bone loss occurring during extraction of the natural tooth.

It is another object of the present invention to provide a dental implant system which possesses the resiliency and limited mobility qualities normally found in a natural tooth.

It is still another object of the present invention to provide a dental implant system which is manufactured practically and which may be implanted routinely by dental surgeon.

It is another object of the present invention to provide a dental implant system which includes a super structure which can be replaced without damage to the implanted root portion.

Yet another object of the present invention is to provide a dental implant system which results in an enhanced cosmetic effect over the implants of the prior art.

Another object of the present invention is to provide a dental implant system which provides a wider load bearing area than prior implants since portions of the missing natural bone has been replaced by artificial bone.

The invention possesses other objects and advantages especially as concerns particular characteristics and features thereof which will become apparent as the specification continues.

BRIEF DESCRIPTION OF THE DRAWINGS

FIG. 1 is a sectional view of the implant system of the present invention permanently affixed to the jawbone.

FIG. 2 is an enlarged sectional view of the right side portion of FIG. 1 showing the dynamics associated with masticatory forces.

FIG. 3 is a sectional view taken along line 3—3 of FIG. 1.

For a better understanding of the invention reference is made to the following detailed description of the preferred embodiments of the invention which should be referenced to the hereinabove described drawings.

DESCRIPTION OF THE PREFERRED EMBODIMENTS

Various aspects of the present invention will evolve from the following detailed description of the preferred embodiments which should be taken in conjunction with the hereinabove described drawings.

With reference to FIG. 1 a dental implant system 10 is shown. The implant system 10 includes, as one of its elements, a root 12 which is fixed to the jawbone 14 in place of an extracted natural tooth. Root 12 may be constructed of titanium, or other relatively rigid material which is compatible with human tissue. Root 12 would be implanted first within jawbone 14 per the techniques described and known in the prior art. Root 12 is generally cylindrical and has an external threaded portion 16 which may be self tapping. In addition, a relatively smooth surface 18 extends from the upper extremity of threaded portion 16 through a lip 20. A recess 22 is formed between threaded portion 16 and 20. It may be apparent that jawbone 14, in FIG. 1 is missing its natural upper portion. This results from the extraction of the natural tooth from jawbone 14 prior to insertion of root 12. Recess 22 formed along surface 18 between lip 20 and the upper portion of jawbone 14 constitutes means 24 for holding artificial bone 26 to root 12. Gingiva 28 grows naturally along the outer surface 30 of jawbone 14 and along the outer surface 32 of artificial bone 26. The appearance of implant 10 becomes cosmetically acceptable as a result of means 24.

Implant 10 also includes a post 34 which is supported to the root 12. Post 34 includes a threaded portion 36 which is located on the lower part 38 thereof. Post 34 possesses an upper part 40 which includes a slot 42 to facilitate the turning of post 40 within root 12. A crown 44, of known construction, may be formed over post 42.

Interposed root 12 and post 34 is means 46 for cushioning forces applied to crown 44. Means 46 may take the form of a resilient member 48 having the first element 50 and a second element 52. First element 50 includes an external threaded portion 54 which threadingly engages the internal threaded portion 56 of root 12. An internally threaded portion 58 of second element 52 threadingly engages the externally threaded portion 36 of post 34. Thus, the first element 50 serves the dual purpose of cushioning forces on crown 34, expecially those having lateral components, and as means for supporting post 34 to root 12. Post 34 may be constructed of materials similar to those used for root 12, such as titanium. On the other hand resilient member 48 could be constructed of plastic like material such as teflon, silicon rubber, and the like. First element 50 of resilient member 48 may be separate from second element 52 or formed as a unitary body. Second element 52 is especially useful in absorbing vertical forces on crown 44. It should be noted that crown 44 within a human jaw could receive forces having both lateral and vertical components.

System 10 further includes means 60 for attenuating relative movement between crown 44 and root 12. Means 60 may embrace the use of a spacer 62 which again may be constructed of material similar to post 34 and root 12. Spacer 62, in the embodiment shown in FIGS. 1 and 2, has a first portion 64 and a second portion 66. First portion 64 of spacer 62 lies between crown 44 and resilient member 48. Second portion 66 of spacer 62 is placed closer to root 12 than first portion 64 thereof. A gap 68 is generally formed between the upper surface 70 of root 12 and the lower surface 72 of second portion 66 of spacer 62. Spacer 62 possesses a degree of resiliency, generally of a lesser degree than member 48.

Turning to the upper part 40 of post 34 it may be seen that a flange 74 is formed which lies immediately adjacent spacer 62. Thus, as slot 42, FIG. 3 is engaged by a turning tool (not shown). Flange 74 compresses spacer 62 which in turn compresses second element 52 of resilient member 48. Gap 68 is formed by sizing spacer 62 and resilient member 48 according to the type of material used for those items. The portion of post 34 may be controlled and measured to provide the proper gap 68 between surfaces 70 and 72. Although the root 12 is shown in the embodiment in FIG. 1 as being bored entirely through the central portion thereof, root 12 may also be constructed with a bottom to limit the downward movement of post 34 to properly form gap 68. It has been found that the natural periodental ligament permits the natural tooth to move about 200 microns.

Turning to FIG. 3 it may be seen that force arrow 73 represents a force that would close gap 68 until second portion 66 of spacer 62 would touch root 12. At this point crown 44 and post 34 would have limited mobility. It should be noted, however, that a groove or/crevice 76 between upper portion 40 of post 34 and flange 74 would permit a small degree of deformation of upper part 40 of post 34. This feature permits the surgeon to adjust upper portion 40 of root 34 to render crown 44 parallel to adjacent teeth. Returning to FIG. 1 it may be seen that a space 78 may be left between artificial bone 26 and jawbone 14. Natural connective tissue may grow in space 78 to aid in the joining of artificial bone section 26 and jawbone 14. Also, this scar tissue adds a degree of resiliency in the implant system 10.

In operation, the surgeon implants root 12 by known surgical techniques. Resilient member 48 is threaded into root 12 and post 34 is threaded within resilient member 48. A spacer 62 is interposed second element 52 of resilient member 48 and root 12. A gap 68 is formed between surfaces 70 and 72 of root 12 and second portion 66 of spacer 62. Upper part 40 of root 34 is bent or formed to permit crown 44 placement paralled to adjacent teeth. Vertical forces on crown 44 during masticatory activity would be absorbed by resilient member 48 and, to a certain extent, first portion 64 spacer 62. Lateral components of any forces on crown 44 would again be absorbed by resilient member 48 and mobility of crown 44 would be limited according to the width of gap 68. Thus the implant system provides for the permanent replacement of a missing bone following a tooth extraction, and a permanent root 12. The super structure comprising the post 34, resilient member 48, spacer 62, and crown 44 may be removed without damaging the implanted root 12.

While in the foregoing embodiments of the present invention have been set forth in considerable detail for the purpose of making a complete disclosure of the invention, it may be apparent to those of skill in the art that numerous changes may be made in such detail without departing from the spirit and principles of the invention.

What is claimed is:

1. A dental implant system intended for placement in an alveolus of the jaw bone comprising:
    a. a root including means intended for fixing the root to the jawbone said root having a portion intended for extending into the alveolus, said root further including a surface having a transverse dimension in relation to said root portion extending into the alveolus, said root surface intended for being adjacent the outer surface of the jawbone;
b. a post including means for supporting said post to said root;
c. a crown connected to said post;
d. means for cushioning forces applied to said crown, said cushioning means including a resilient member having a first element placed between said post and said portion of said root intended for extending into the alveolus; and a second element placed adjacent said surface of said root adjacent the outer surface of the jawbone; and
e. means for attenuating relative movement between said crown and said root upon the application of force to said crown, said attenuating means including a spacer disposed adjacent said second element of said resilient member such that said second element of said resilient member lies between said surface of said root adjacent the outer surface of the jawbone and said spacer, said spacer including a surface intended for being capable of directly contacting said root surface adjacent the outer surface of said jawbone, thereby attenuating the relative movement between said crown and said root.

2. The dental implant system of claim 1 in which said spacer further includes a first portion disposed between said crown and said first element of said resilient member, and includes a second portion lying closer to said root surface adjacent the outer surface of the jawbone than said first portion of said spacer, said second portion of said spacer including said surface being capable of directly contacting said root surface adjacent the outer surface of the jawbone.

3. The dental implant system of claim 2 in which said surface of said spacer second portion lies adjacent to and apart from said root surface adjacent the outer surface of the jawbone in the absence of force upon said crown.

4. The dental implant system of claim 1 in which said first and second elements of said resilient member form an integral unit.

5. The dental implant system of claim 1 in which said post further includes a flange lying adjacent said spacer, and a crevice between said flange and said post, said post being movable in relation to said root.

6. The dental implant system of claim 1 in which said root further comprises means for holding artificial bone to said root.

7. The dental implant system of claim 6 in which said means for holding artificial bone to said root comprises a recessed portion formed on said root adjacent the jawbone.

8. A dental implant system for placement in an aveolus of the jaw comprising:
a. a root including means intended for fixing the root to the jawbone; said root having a first portion intended for extending into the aveolus and a second portion outside the aveolus adjacent the jaw bone;
b. a post including means for supporting said post to said root;
c. a crown connected to said post;
d. means for cushioning forces applied to said crown; and
e. means for holding artificial bone to said second portion of said root adjacent the jawbone outside of the aveolus, said holding means comprising a lip formed on said root and extending radially from said root, and artificial bone held to said root by said holding means.

9. The dental implant system of claim 8 in which said means for holding artificial bone to said root additionally comprises a recessed portion formed on said root adjacent the jawbone.

* * * * *